USO05533618A

United States Patent [19]
Pickels, Jr.

[11] Patent Number: 5,533,618
[45] Date of Patent: Jul. 9, 1996

[54] SURGICAL HOLSTER

[76] Inventor: Robert F. Pickels, Jr., 4621 E. Seneca Ave., Sherrill, N.Y. 13461

[21] Appl. No.: 321,412

[22] Filed: Oct. 11, 1994

[51] Int. Cl.⁶ .................................................. B65D 83/10
[52] U.S. Cl. .......................... 206/363; 206/464; 206/465; 206/477; 206/526; 224/675; 224/901.4
[58] Field of Search .................................. 206/363, 443, 206/461, 462, 464, 465, 471, 473, 477, 483, 526, 614, 625; 224/252, 253

[56] References Cited

U.S. PATENT DOCUMENTS

| | | |
|---|---|---|
| 1,711,594 | 5/1929 | Gillespie . |
| 2,058,542 | 10/1936 | Wise ........................................ 206/482 |
| 3,404,774 | 10/1968 | Levine ..................................... 206/464 |
| 3,414,159 | 12/1968 | Murr ....................................... 206/465 |
| 3,550,769 | 12/1970 | Wolk ...................................... 206/461 |
| 3,809,226 | 5/1974 | Ferrari .................................... 206/461 |
| 4,244,660 | 1/1981 | Aronson ................................. 206/443 |
| 4,508,225 | 4/1985 | Ferrari .................................... 206/461 |
| 4,689,103 | 8/1987 | Elarde . |
| 4,793,483 | 12/1988 | Holmes . |
| 4,820,658 | 4/1989 | Gilder et al. . |
| 4,859,423 | 8/1989 | Perlman . |
| 4,899,730 | 2/1990 | Stennert et al. . |
| 5,005,590 | 4/1991 | Eldridge, Jr. et al. . |
| 5,020,665 | 6/1991 | Bruno . |
| 5,052,369 | 10/1991 | Johnson . |
| 5,353,930 | 10/1994 | Berry, Jr. . |
| 5,360,110 | 11/1994 | Hirai et al. .............................. 206/714 |

FOREIGN PATENT DOCUMENTS

| | | | |
|---|---|---|---|
| 1304379 | 10/1962 | France ................................... 224/253 |
| 4300385 | 8/1993 | Germany .............................. 206/477 |
| 8000689 | 4/1980 | WIPO .................................... 206/464 |

*Primary Examiner*—David T. Fidei
*Attorney, Agent, or Firm*—Harris Beach & Wilcox

[57] ABSTRACT

A reusable surgical device which is suitable for carrying elongated surgical instruments having a backing plate which supports a plurality of detachable receptacle members contained on the backing plate in fixed engagement. The device is made of a transparent thermoplastic which is electrically insulating, nonflammable, and which can be sterilized at temperatures above 300° F.

3 Claims, 3 Drawing Sheets

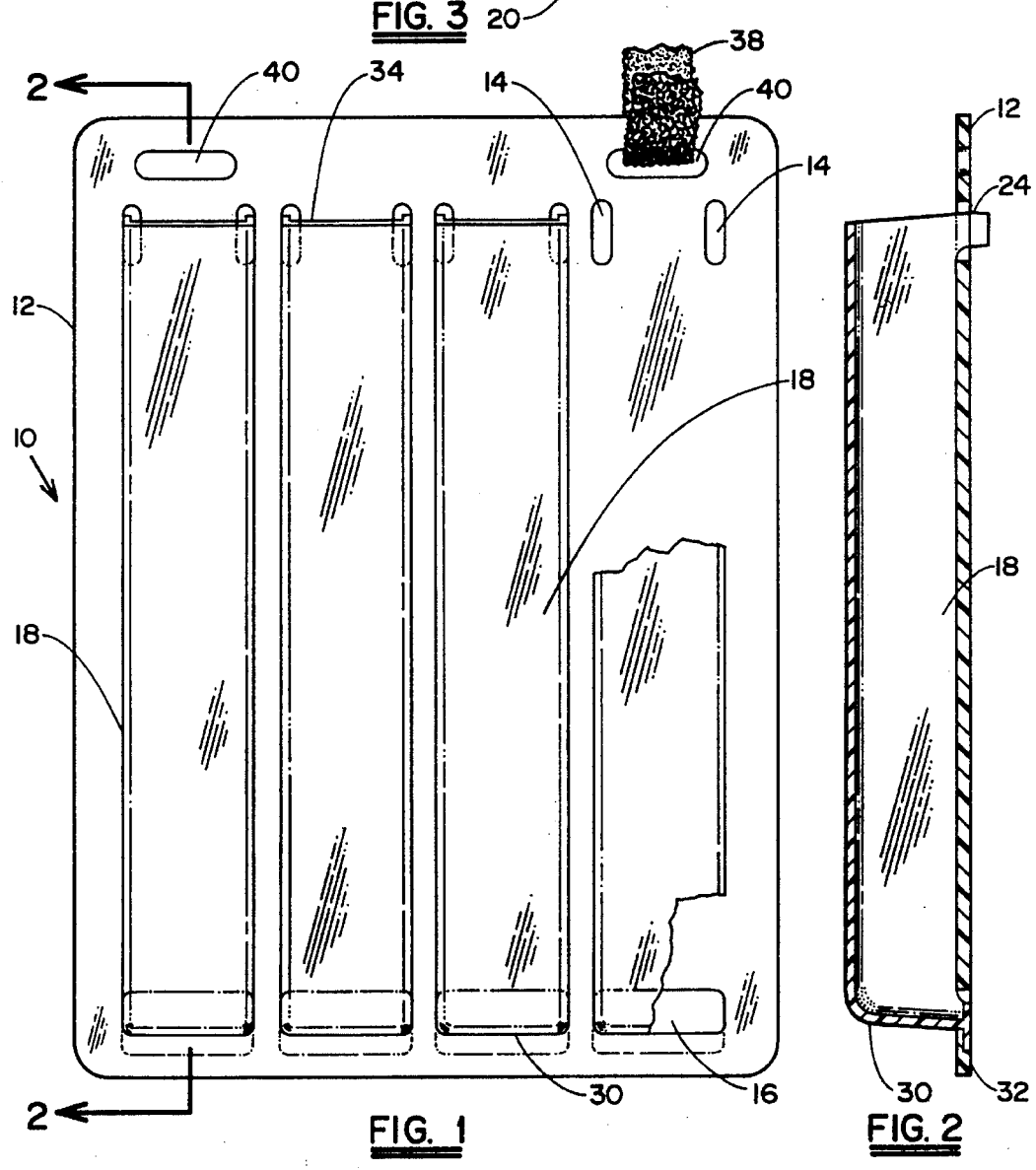

SURGICAL HOLSTER

BACKGROUND OF THE INVENTION

The present invention in general relates to a device for holding instruments and more specifically for surgical instruments used with a laparoscope when carrying out Minimal Invasive Surgery (MIS).

Currently in Minimal Invasive Surgery the operatory utilizes a surgical table on which instruments such as laparoscopic scissors, laparoscopic graspers, laparoscopic hemeclip applicators, and the like are generally placed and made ready for use at the appropriate time when called upon to be used during a laparoscopic procedure. Generally, an attending nurse usually hands a particular instrument to the surgeon performing the operation at the request of the surgeon. When a new instrument is required, the nurse receives the instrument being used from the surgeon, and hands him the next requested instrument. Because of the currently existing conventional procedures, injuries to patients have occurred due to the fact that surgical instruments have been placed on or adjacent the patient following use, due to lack of ordered procedures, and/or the inconvenience of conventional protocol. For example, current carrying instruments such as lasers and cauteries have caused fires in the operatory due to the instruments coming in contact with a flammable material such as a drape. In addition, the placement of the instrument table in the operatory is usually to the back of the surgeon whose attention is being directed to a patient, and therefore the surgeon must repeatedly turn while conducting a given procedure and is not aware of the location of the instruments except upon request to the attending nurse.

In view of the conventional techniques and protocols currently used in operating rooms during laparoscopic procedures, injuries have occurred due to the lack of order in accounting for the location of the surgical instruments being used in these procedure. In addition, manpower in the form of at least one attending nurse is required for the task of handing the particular instrument to the surgeon during a given procedure.

In the area of MIS there has long been a need for a system and/or device which accurately and reliably positions the various instruments used for a given surgical procedure, and allows the surgeon to accurately account for each instrument used during the procedure.

It is therefore an object of the present invention to provide for a reusable surgical holster which stores and presents instruments used in a surgical procedure in a ready position and in an ordered manner to provide the surgeon with a convenient portable workstation which securely holds and accounts for each tool or instrumentor used in a given surgical procedure.

SUMMARY OF THE INVENTION

The present invention provides for an inexpensive, reusable surgical holster designed to hold the necessary instruments and tools used with a laparoscope when carrying out Minimal Invasive surgery (MIS).

The device comprises a backing support plate which contains a plurality of elongated tubular compartments arranged side by side substantially parallel to each other. The compartments are of standard length to accommodate instruments used in minimal invasive surgery, and are removably attached to the backing plate in fixed engagement when the device is in use.

The holster is preferably made of a durable transparent plastic material which is electrically insulating, non-flammable, impervious to lasers, and which can be easily cleaned and sterilized at temperatures above 350° F. for indefinite further reuse. The holster optionally contains attachment means such as, for example, straps or clips which enable the device to be attached to and/or draped over a stand or table or any other convenient support means, allowing it to hang down.

BRIEF DESCRIPTION OF THE DRAWINGS

FIG. 1 is a front view of one embodiment of the present invention.

FIG. 2 is a sectional side view of the device of FIG. 1, along line 2—2.

FIG. 3 is a top view of the device of FIG. 1.

DETAILED DESCRIPTION OF THE INVENTION

Figure 4:
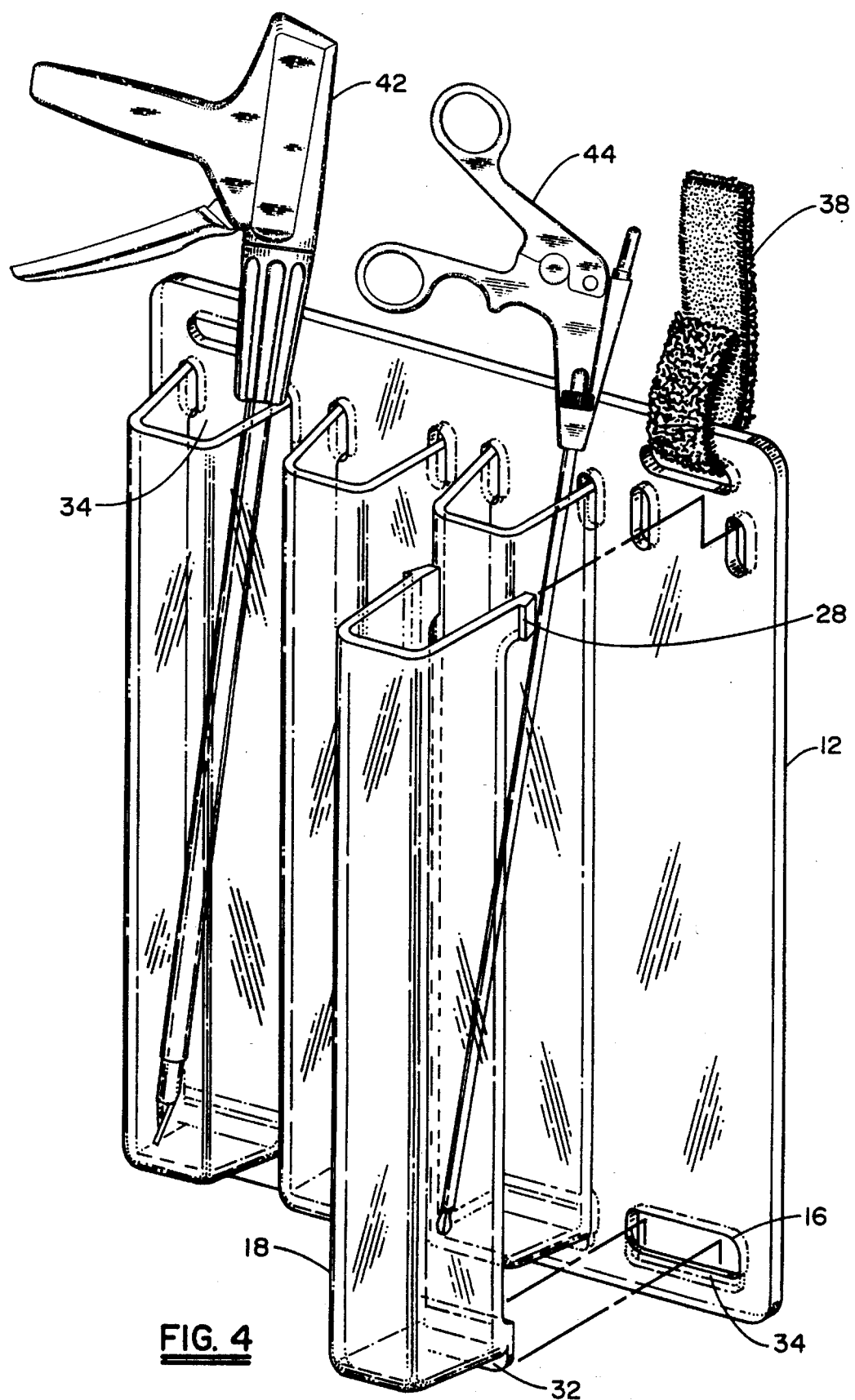
FIG. 4 is a perspective view of the device of FIG. 1.

Referring to FIG. 4 of the drawings, which is a perspective view of the device of the present invention, it can be seen that the device comprises a backing or support plate which contains a plurality of elongated tubular receptacles or compartments which are affixed to the support plate and arranged side-by-side substantially parallel with each other. More specifically, as illustrated in FIG. 1 of the drawings, the device 10 comprises a backing plate 12 which contains a plurality of upper paired slots 14 suitable for receiving locking means to be described more specifically herein. Backing plate 12 further contains a plurality of bottom slots 16 which in the embodiment illustrated, constitutes one horizontal slot for each corresponding pair of upper slots 14. A plurality of detachable receptacle members 18, designed for fixed engagement to backing plate 12 utilize a pair of upper locking tabs 24 each of which contain a bevelled surface 26 and a vertical locking surface 28. Receptacle members 18 contain side walls 20 integrally connected with a front wall 22 and an enclosed bottom wall 30 which seals both side walls 20 and front wall 22. Bottom wall 30 further contains, integral therewith, locking tab 32 which extends vertically below bottom wall 30. Lower slot 16 in backing plate 14 further contains a recessed section 34 below the bottom edge of slot 16 which has a depth which approximately equals the thickness of the tab 32. As shown more clearly in FIG. 4, the receptacle member generally has a c-shaped configuration with one open vertical side wall.

In operation, the receptacle member 18 is designated so that the protruding top portion defined by tabs 24 is slightly wider than the width defined by a given pair of vertical top slots 14, which is more clearly shown in FIG. 4. In attaching receptacle 18 in fixed engagement to backing plate 12, lower locking tab 32 is first inserted down into lower slot 16. The lower portion of tab 32 locks in place within recess 34 and the detachable receptacle member is then pivoted forward into final locking engagement by slightly pressing the two tabs 24 together and snap fitting both tabs 24 into a pair of upper slots 14. Bevelled surfaces 26 allow the tabs to slide freely through the sides of slots 14, and when passing through the slot thickness lock the receptacle member in place against the vertical locking surfaces 28 of tab 24. Due to the expanded tensional force on side walls 20 due to the fact that the resilient plastic material is sized slightly wider than the widths between paired slots 14 is of sufficient tension to hold receptacle in place in conjunction with lower locking tab 32.

When locked in place, (FIGS. 2, 3, 5 and 6) receptacle member 18, in conjunction with the surface of backing plate 12, defines an enclosed receptacle having an open top 34 which is suitable for holding and presenting surgical instruments 42 and 44 in a secure and convenient manner.

Figure 5:
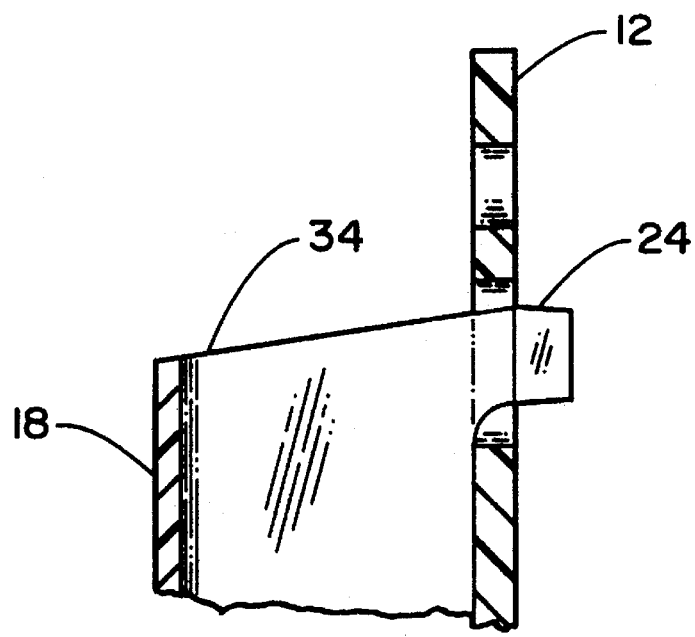
FIG. 5 is an enlarged view of the top section of the device shown in FIG. 2.
Figure 6:
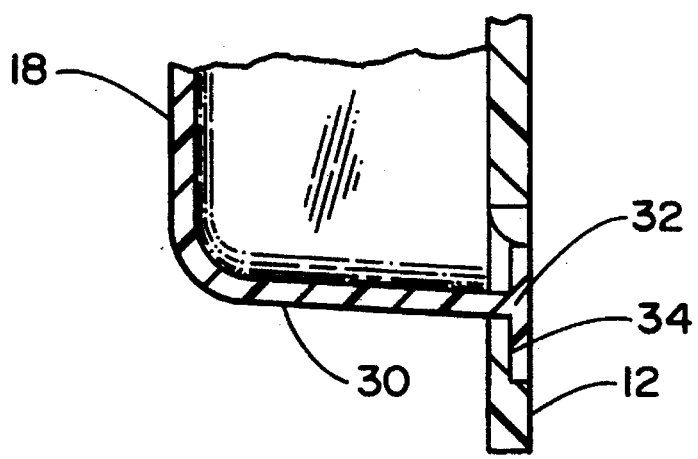
FIG. 6 is an enlarged view of the bottom section of the device shown in FIG. 2.

FIGS. 5 and 6 show in greater detail the structure and relationship of the top and bottom looking tabs with respect to the slots contained in the backing plate.

The backing plate and receptacle member are preferably made of a durable plastic material, usually an injection moldable thermoplastic. A particularly preferred material comprises a transparent polyetherimide available under the trademark Ultem® from General Electric Company. This material exhibits the required properties for the device of the present invention which are that the device electrically insulating, laser impervious, nonflammable and exhibits high temperature stability (up to 380° F.) for sterilization.

Upon completion of a given surgical procedure, the device of the present invention may be disassembled by squeezing the two upper tabs together and pulling the top of the receptacle away from the backing plate, and then up, to release the bottom locking tab 32, resulting in the removal of the attachable receptacle member from the backing plate. This structure allows the components of the device to be easily cleaned and later sterilized for further reuse. If the receptacle members were not detachable and made integral with the back wall, the device would be extremely difficult to clean and almost impossible to sterilize with any degree of reliability to allow the device to be reused an indefinite number of times. In addition, should any given receptacle member be damaged or lost, it can simply be replaced with a new receptacle without having to replace or scrap the entire device.

The device of the present invention can be attached to any convenient location, such as a mayo stand, within a surgeon's immediate reach. In one embodiment, straps 38 contained in slots 40 can be used to attach the device to any convenient support means. Instead of requiring the need for the surgeon to receive instruments from a scrub nurse, the device allows the surgeon to quickly pull out and then return instruments almost at a glance. The device therefore eliminates the need for the second nurse usually required in performing laparoscopic surgery. Furthermore, because the instrument reduces the number of people handling instruments, it lessens the chance of dropping them or prevents or almost entirely eliminates instruments being damaged and therefore having to be replaced. Through the use of a suitable thermoplastic material the device of the present invention is electrically insulated, flame retardant and non-conductive. Because the device of the present invention securely stores all of the instruments, it also reduces risk of injury to the patient and the operating staff. The instrument is simple to clean due to the detachable receptacle sections, and is suitable for sterilization using either gas or heat, and can be reused indefinitely providing for great economy.

Further advantages are that the surgeon no longer must repeatably reach or twist around to be handed instruments, and the instruments are presented and viewed by the surgeon in an order manner in that with the plastic being substantially transparent, the instruments are easily seen by the surgeon.

While this invention has been explained with reference to the structure disclosed herein, it is not confined to the details set forth and this application is intended to cover any modifications and changes as may come within the scope of the following claims:

I claim:

1. A reusable surgical device suitable for carrying elongated surgical instruments which comprises a backing plate having a plurality of elongated detachable receptacle members contained on said backing plate in fixed engagement, wherein said backing plate contains a plurality of slots through the thickness of said backing plate and wherein each of said receptacle members contains a plurality of locking tabs configured to fit into said slots in locking engagement, said receptacle members having an opening defined by a pair of substantially vertical edges, said receptacle members further having an open top and a closed bottom, with said vertical edges abutting against the surface of said backing plate, and where said receptacle members and said backing plate together define a plurality of enclosed elongated chambers having an open top that removably receive surgical instruments.

2. The device of claim 1 in which the backing plate and chamber are made of a transparent, electrical insulating, nonflammable thermoplastic which can be sterilized at temperatures above 300° F.

3. The device of claim 2 in which the plastic comprises a polyetherimide.

\* \* \* \* \*